US011013866B2

(12) United States Patent
Harman

(10) Patent No.: US 11,013,866 B2
(45) Date of Patent: May 25, 2021

(54) KNIFE WITH MANUAL SYRINGE HUB REMOVER

(71) Applicant: Hawkeye Bits and Spurs, LLC., Norcatur, KS (US)

(72) Inventor: Scotty Hawkeye Harman, Norcatur, KS (US)

(73) Assignee: HAWKEYE BITS AND SPURS, LLC, Norcatur, KS (US)

( * ) Notice: Subject to any disclaimer, the term of this patent is extended or adjusted under 35 U.S.C. 154(b) by 257 days.

(21) Appl. No.: 16/415,045

(22) Filed: May 17, 2019

(65) Prior Publication Data

US 2020/0108208 A1 Apr. 9, 2020

Related U.S. Application Data

(60) Provisional application No. 62/740,733, filed on Oct. 3, 2018.

(51) Int. Cl.
*A61M 5/32* (2006.01)
*B26B 11/00* (2006.01)
*B26B 3/00* (2006.01)

(52) U.S. Cl.
CPC ............. *A61M 5/3205* (2013.01); *B26B 3/00* (2013.01); *B26B 11/00* (2013.01)

(58) Field of Classification Search
CPC ........ A61M 5/3205; B26B 3/00; B26B 11/00; B26B 11/006
See application file for complete search history.

(56) References Cited

U.S. PATENT DOCUMENTS

| | | | | |
|---|---|---|---|---|
| 4,442,559 A | * | 4/1984 | Collins | B26B 3/06 30/153 |
| D398,211 S | * | 9/1998 | Howard | D22/118 |
| 8,695,138 B2 | * | 4/2014 | Pelton | B26B 1/00 7/118 |
| 8,707,490 B1 | * | 4/2014 | Pelton | B26B 3/00 7/156 |
| 10,207,415 B2 | * | 2/2019 | Vellekamp | A45F 5/021 |
| 2009/0277015 A1 | * | 11/2009 | Duey | B26B 1/046 30/160 |
| 2018/0311804 A1 | * | 11/2018 | Weinberger | B25B 13/56 |
| 2019/0329430 A1 | * | 10/2019 | Billado, Jr. | B26B 5/00 |
| 2019/0337169 A1 | * | 11/2019 | Wang | B26B 11/003 |

\* cited by examiner

*Primary Examiner* — David B. Thomas

(74) *Attorney, Agent, or Firm* — Berg Hill Greenleaf Ruscitti LLP.

(57) ABSTRACT

The invention may include a knife having a syringe hub remover. In one embodiment, the invention may include a hub slot that may be integral to the knife tang and that may further be configured to be positioned over a syringe hub and allow for an improved leveraged torque force to be applied thereby twisting and ultimately assisting in the removal of the syringe hub.

20 Claims, 3 Drawing Sheets

KNIFE WITH MANUAL SYRINGE HUB REMOVER

CROSS-REFERENCE TO RELATED APPLICATION

This application claims the benefit of and priority to U.S. Provisional Application No. 62/740,733, filed Oct. 3, 2018. The entire specification and figures of the above-referenced application is hereby incorporated in its entirety by reference.

TECHNICAL FIELD

The invention relates to a medical assistive device, and in particular a medical assistive device configured to remove the needle securing hub of a syringe that may be used in large animal medical procedures.

BACKGROUND

In the treatment of livestock and other commercial wildlife populations it is often necessary to administer vaccines or other medicines through a conventional syringe device. While such convention syringes have been used by farmers, ranchers and wildlife management professionals for decades certain practical limitations are present that limit their safe and efficient use. For example, as described in more detail below, a typical livestock syringe may require a large gauge needle to penetrate an animal's hide and thick muscle tissue. Such large gauge needs often need to be replaced or removed from the syringe after, or even between uses to prevent cross-contamination.

However, such large gauge needles often become stuck and are difficult to remove by hand. This problem also endangers the user's safety as it requires the manual placement of a user's hand on the needle hub which may raise direct and cross-contamination concerns, as well as heightening the risk that a user may be accidently pricked by the needle potentially transmitting disease and other potentially harmful contaminates.

As can be seen, there is a need for a single comprehensive solution to the problems associate with livestock syringes described above. It is therefore the object of the present invention to provide a cost effective and durable, syringe hub removal system that can be easily employed in the field. Naturally, further objects of the inventive technology will become apparent from the description and drawings below.

SUMMARY OF THE INVENTION

One aspect of the invention may include a knife having a syringe hub remover. In this aspect, the invention may include a hub slot that may be integral to the knife tang and that may further be configured to be positioned over a syringe hub and allow for an improved leveraged torque force to be applied thereby twisting and ultimately assisting in the removal of the syringe hub.

Additional aspects of the invention may include:

1. A modified knife comprising a handle configured to be coupled with a knife blade tang wherein said knife tang further comprises a syringe hub remover having at least one hub slot configured to be positioned over a syringe hub at the distal end of a syringe needle and allow for an improved leveraged torque force to remove said syringe hub.

2. The modified knife of embodiment 1 wherein said syringe hub remover is integral with said knife tang.

3. The modified knife of embodiment 1 wherein said syringe hub remover is detachable.

4. The modified knife of embodiment 1 wherein said hub slot further comprises two substantially parallel surfaces joined by a substantially horizontal surface configured to be positioned over a syringe hub.

5. The modified knife of embodiment 1 wherein said syringe hub remover is positioned facing the edge surface of the knife blade.

6. The modified knife of embodiment 1 wherein said syringe hub remover is positioned facing the edge surface of the knife blade.

7. The modified knife of embodiment 1 wherein said syringe hub remover further comprises a guard.

8. The modified knife of embodiment 1 wherein said syringe hub is from a syringe used to vaccinate large agricultural animals.

9. A modified knife comprising a knife handle having at least one syringe hub remover having at least one hub slot configured to be positioned over a syringe hub at the distal end of a syringe needle and allow for an improved leveraged torque force to remove said syringe hub.

10. The modified knife of embodiment 9 wherein said syringe hub remover is integral with said handle.

11. The modified knife of embodiment 9 wherein said syringe hub remover is detachable.

12. The modified knife of embodiment 9 wherein said hub slot further comprises two substantially parallel surfaces joined by a substantially horizontal surface configured to be positioned over a syringe hub.

13. The modified knife of embodiment 9 wherein said syringe hub remover is positioned facing the edge surface of the knife blade.

14. The modified knife of embodiment 9 wherein said syringe hub remover is positioned facing the edge surface of the knife blade.

15. The modified knife of embodiment 9 wherein said syringe hub remover further comprises a guard.

16. The modified knife of embodiment 9 wherein said syringe hub is from a syringe used to vaccinate large agricultural animals.

17. A modified knife comprising at least one syringe hub remover having at least one hub slot configured to be positioned over a syringe hub and allow for an improved leveraged torque force to remove said syringe hub.

18. The modified knife of embodiment 17 wherein said syringe hub remover is selected from the group consisting of: an integral syringe hub remover and a detachable syringe hub remover.

19. The modified knife of embodiment 17 wherein said hub slot further comprises two substantially parallel surfaces joined by a substantially horizontal surface configured to be positioned over a syringe hub.

20. The modified knife of embodiment 17 wherein said syringe hub remover is selected from the group consisting of: a syringe hub remover positioned facing the edge surface of the knife blade forming a guard, and a syringe hub remover is positioned facing the edge surface of the knife blade forming a guard.

BRIEF DESCRIPTION OF DRAWINGS

The novel aspects, features, and advantages of the present disclosure will be better understood from the following detailed descriptions taken in conjunction with the accompanying figures, all of which are given by way of illustration only, and are not limiting the presently disclosed embodiments, in which.

DETAILED DESCRIPTION OF INVENTION

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Figure 1:
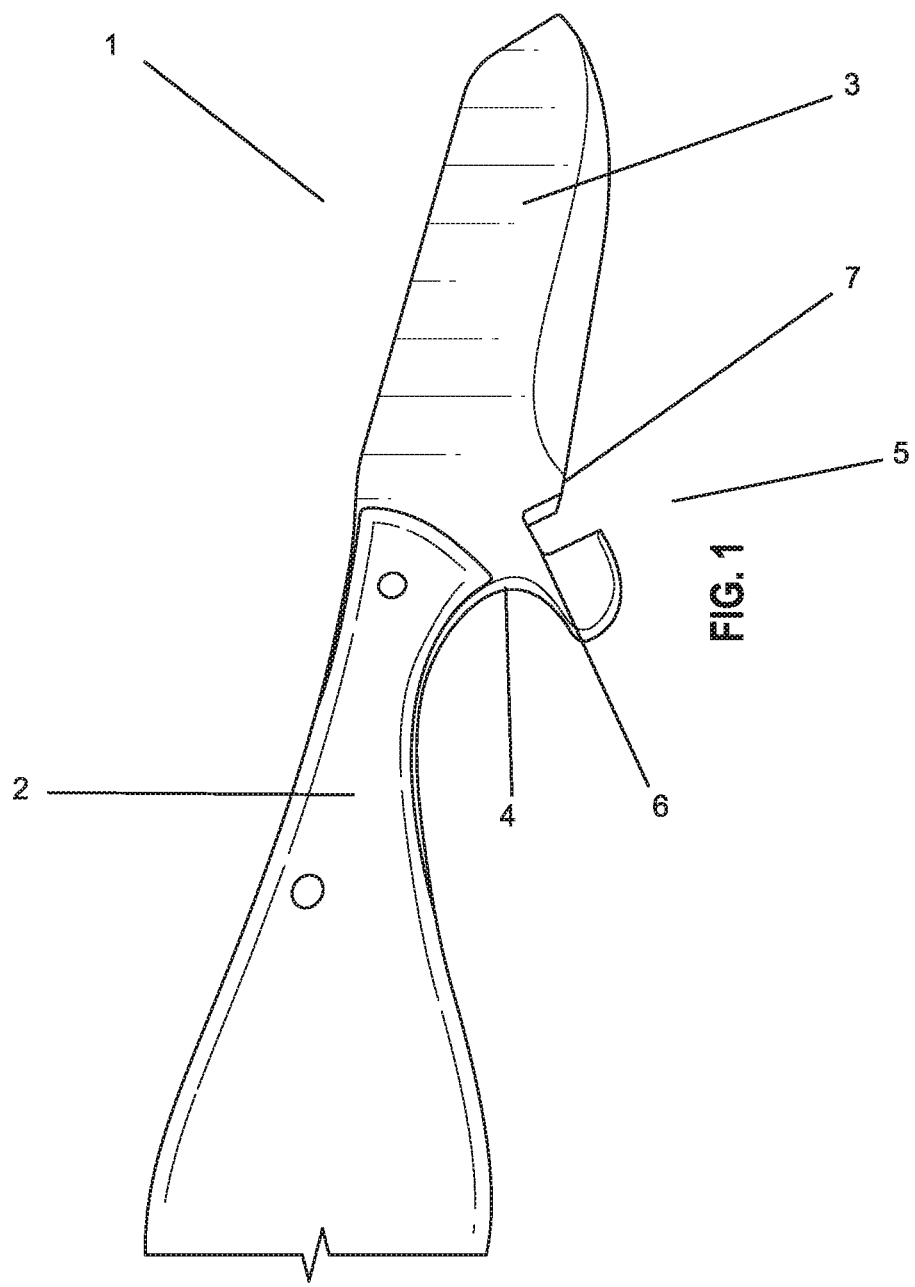
FIG. 1—demonstrates a knife having a syringe hub remover in one embodiment thereof.
Figure 2:
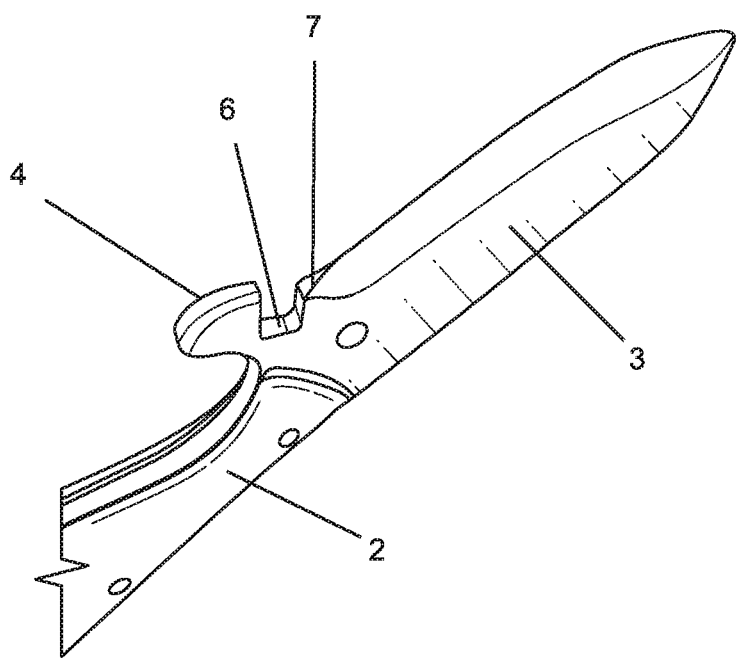
FIG. 2—demonstrates a knife having a syringe hub remover in one embodiment thereof.

As generally shown in FIGS. 1-4, the invention may include a knife (1) having a syringe hub remover (5). As shown in this preferred embodiment, the exemplary knife (1) may include a knife blade body (3) having a tang (7) that may be secured to a handle (2). The syringe hub remover (5) in this embodiment may be formed as part of, or integral with the knife's tang. As shown in FIG. 1, the syringe hub remover (5) may be positioned on the underside of the knife (1) at approximately the position of a typical knife handle along the edge surface. In one embodiment, the syringe hub remover (5) may be positioned near the knife heel. It should be noted that this is merely one example of the placement of the syringe hub remover (5). For example, in alternative embodiments, a syringe hub remover (5) may be positioned along the top leading edge of the knife, or the spine, or even on the end of the handle (2).

Figure 3:
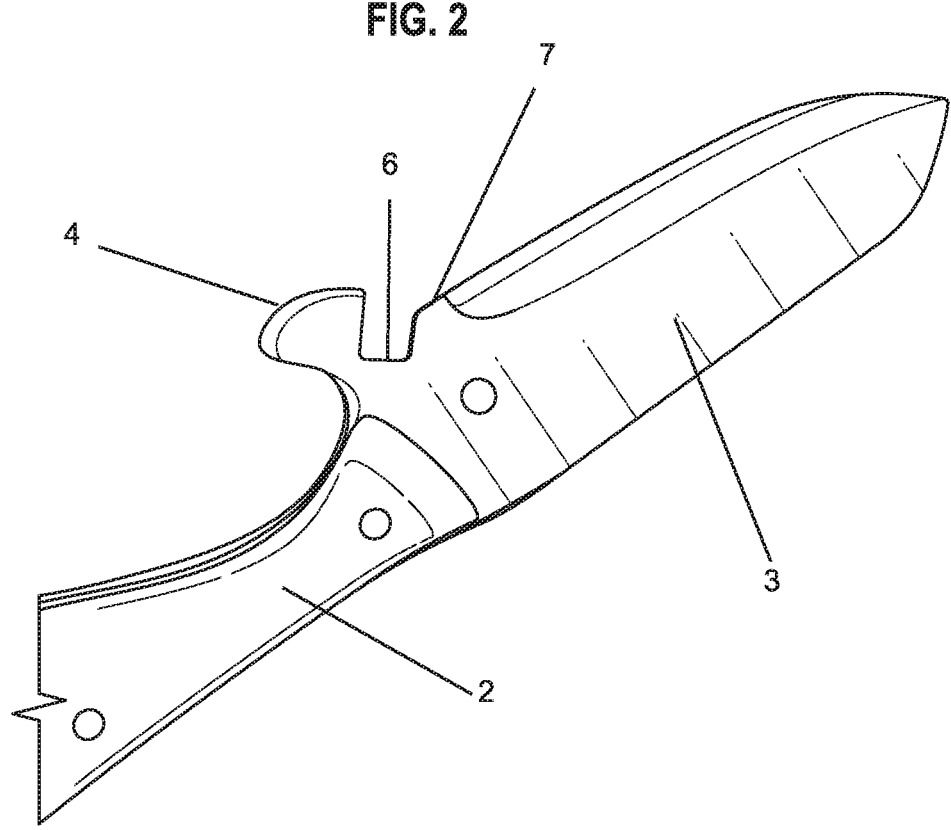
FIG. 3—demonstrates a knife having a syringe hub remover in one embodiment thereof.
Figure 4:
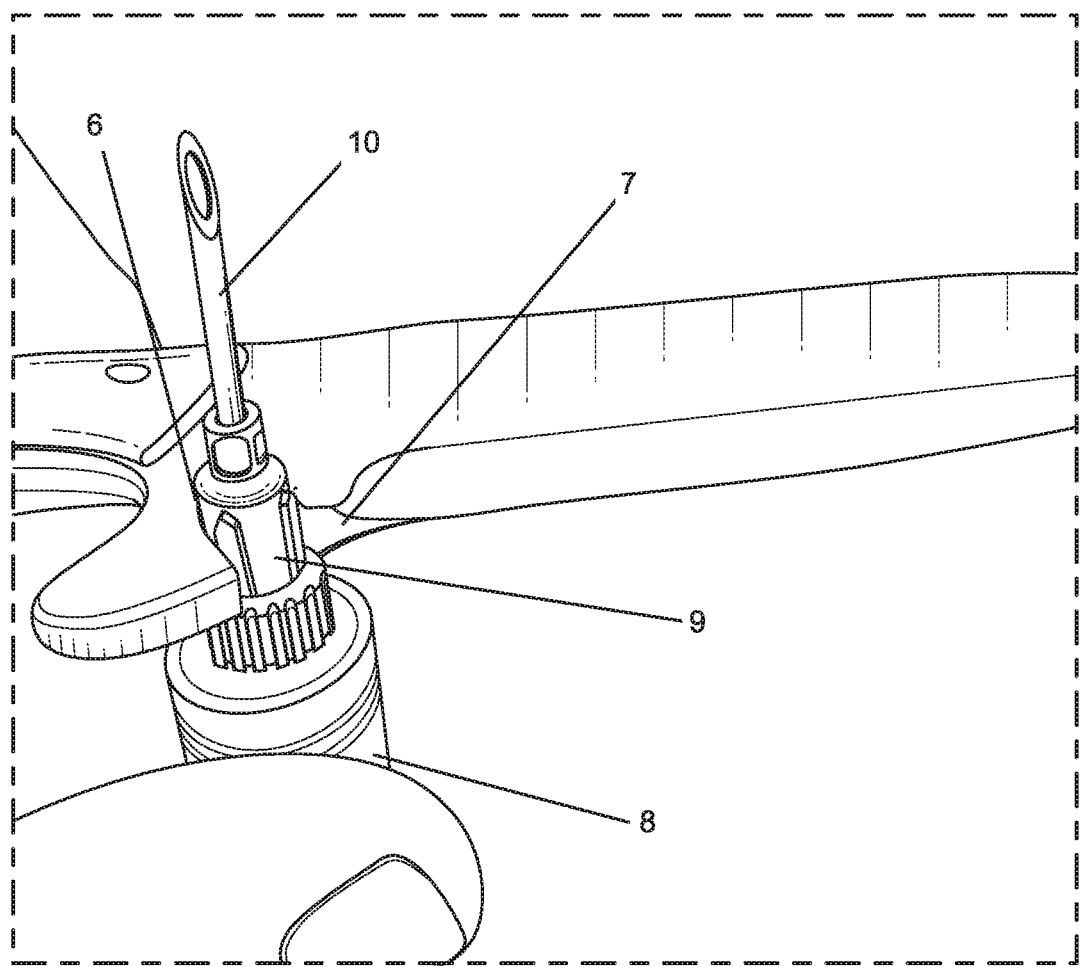
FIG. 4—demonstrates a knife having a syringe hub remover securing a syringe hub in one embodiment thereof.

Referring to FIG. 3, in this embodiment a syringe hub remover (5) may be formed from a shaped extension which again, may be integral with the knife's tang or be separately attachable to the knife, such as to the handle or guard portion of the knife. In this embodiment, the syringe hub remover (5) may be formed by an outward extension of the tang and may further form a guard (4) position. This guard position may further be configured to accommodate a user's index finger or other similar such anatomical accommodating structure.

Referring back to FIG. 2, a syringe hub remover (5) may be configured to have a hub slot (6). In the preferred embodiment shown in the FIG. 4, this hub slot (6) may be configured to be positioned around a syringe hub (9) at a position distal to the syringe needle (10). While the figures show a hub slot (6) having two substantially parallel surfaces joined by a substantially horizontal surface, a variety of configurations may be used which may be adaptable to a variety of syringe hub (6) shapes and sizes.

Again referring to FIG. 4, in this embodiment a syringe (8) having a syringe hub (9) and needle (10) may be used, for example to vaccinate livestock or other large animals or wildlife. A user may then position the hub slot (6) of the syringe hub remover (5) over the syringe hub (9) and use the handle (2) to provide a leveraged torque force to twist and ultimately remove the syringe hub (9). This particular embodiment may be especially useful where the syringe hub may be stuck, or in other situations where it would be important to remove the syringe hub (9) without having to touch it and potentially cause cross-contamination or the spread of blood or tissue borne animal pathogens. As can be seen in the figures and disclosure, the invention may also be used as a device to secure or tighten a syringe hub (9) to a syringe (8) in a similar, albeit opposing manner as generally described herein.

Naturally, all embodiments discussed herein are merely illustrative and should not be construed to limit the scope of the inventive technology consistent with the broader inventive principles disclosed. As may be easily understood from the foregoing, the basic concepts of the present inventive technology may be embodied in a variety of ways. It generally involves systems, methods, and techniques as well as devices to accomplish a knife having a manual syringe hub remover system. In this application, the techniques, including novel and unique uses of manufacturing methods and materials, are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the inventive technology and may not explicitly show how each feature or element can actually be representative of a broader function or of a great variety of alternative or equivalent elements. Again, these are implicitly included in this disclosure. Where the inventive technology is described in device-oriented terminology, each element of the device implicitly performs a function. Apparatus claims may not only be included for the device described, but also method or process claims may be included to address the functions the inventive technology and each element performs. Neither the description nor the terminology is intended to limit the scope of the claims that will be included in any subsequent patent application.

It should also be understood that a variety of changes may be made without departing from the essence of the inventive technology. Such changes are also implicitly included in the description. They still fall within the scope of this inventive technology. A broad disclosure encompassing both the explicit embodiment(s) shown, the great variety of implicit alternative embodiments, and the broad apparatus, methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the inventive technology both independently and as an overall system.

Further, each of the various elements of the inventive technology and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the inventive technology, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this inventive technology is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of an "syringe hub remover" should be understood to encompass disclosure of the act of "removing a syringe hub"—whether explicitly discussed or not—and, conversely, were there effectively disclosure of the act of "removing a syringe hub", such a disclosure should be understood to encompass disclosure of "a syringe hub method and/or technique, and or device." Such changes and alternative terms are to be understood to be explicitly included in the description.

Thus, the applicant(s) should be understood to have support to claim and make a statement of invention to at least: i) each of the methods, apparatus, improvements and/or devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, xii) each potentially dependent claim or concept as a dependency on each and every one of the independent claims or concepts presented, and xiii) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in Hakim v. Cannon Avent Group, PLC, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like.

Finally, any claims set forth at any time are hereby incorporated by reference as part of this description of the inventive technology, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A modified knife comprising a handle configured to be coupled with a knife blade tang wherein said knife tang further comprises a syringe hub remover having at least one hub slot configured to be positioned over a syringe hub at the distal end of a syringe needle and allow for an improved leveraged torque force to remove said syringe hub.

2. The modified knife of claim 1 wherein said syringe hub remover is integral with said knife tang.

3. The modified knife of claim 1 wherein said syringe hub remover is detachable.

4. The modified knife of claim 1 wherein said hub slot further comprises two substantially parallel surfaces joined by a substantially horizontal surface configured to be positioned over a syringe hub.

5. The modified knife of claim 1 wherein said syringe hub remover is positioned facing the edge surface of the knife blade.

6. The modified knife of claim 1 wherein said syringe hub remover is positioned facing the edge surface of the knife blade.

7. The modified knife of claim 1 wherein said syringe hub remover further comprises a guard.

8. The modified knife of claim 1 wherein said syringe hub is from a syringe used to vaccinate large agricultural animals.

9. A modified knife comprising a knife handle having at least one syringe hub remover having at least one hub slot configured to be positioned over a syringe hub at the distal end of a syringe needle and allow for an improved leveraged torque force to remove said syringe hub.

10. The modified knife of claim 9 wherein said syringe hub remover is integral with said handle.

11. The modified knife of claim 9 wherein said syringe hub remover is detachable.

12. The modified knife of claim 9 wherein said hub slot further comprises two substantially parallel surfaces joined by a substantially horizontal surface configured to be positioned over a syringe hub.

13. The modified knife of claim 9 wherein said syringe hub remover is positioned facing the edge surface of the knife blade.

14. The modified knife of claim 9 wherein said syringe hub remover is positioned facing the edge surface of the knife blade.

15. The modified knife of claim 9 wherein said syringe hub remover further comprises a guard.

16. The modified knife of claim 9 wherein said syringe hub is from a syringe used to vaccinate large agricultural animals.

17. A modified knife comprising at least one syringe hub remover having at least one hub slot configured to be positioned over a syringe hub and allow for an improved leveraged torque force to remove said syringe hub.

18. The modified knife of claim 17 wherein said syringe hub remover is selected from the group consisting of: an integral syringe hub remover and a detachable syringe hub remover.

19. The modified knife of claim 17 wherein said hub slot further comprises two substantially parallel surfaces joined by a substantially horizontal surface configured to be positioned over a syringe hub.

20. The modified knife of claim 17 wherein said syringe hub remover is selected from the group consisting of: a syringe hub remover positioned facing the edge surface of the knife blade forming a guard, and a syringe hub remover is positioned facing the edge surface of the knife blade forming a guard.

* * * * *